United States Patent [19]

Robbins

[11] Patent Number: 4,478,755

[45] Date of Patent: Oct. 23, 1984

[54] TITANATE COMPOSITIONS HAVING DEPRESSED FREEZING POINTS

[75] Inventor: Gordon B. Robbins, Claymont, Del.

[73] Assignee: E. I. Du Pont de Nemours and Company, Wilmington, Del.

[21] Appl. No.: 439,566

[22] Filed: Nov. 5, 1982

[51] Int. Cl.$^3$ .............................................. C07F 7/28
[52] U.S. Cl. .................................................. 260/429.5
[58] Field of Search ..................................... 260/429.5

[56] References Cited

U.S. PATENT DOCUMENTS

| | | | |
|---|---|---|---|
| 3,387,994 | 6/1968 | Dunton et al. | 260/429.5 X |
| 3,856,839 | 12/1974 | Smith et al. | 260/429.5 X |
| 4,313,851 | 2/1982 | Barfurth et al. | 260/429.5 X |

OTHER PUBLICATIONS

Feld et al., The Organic Chemistry of Titanium, Butterworths, Wash., D.C., pp. 21, 31, 35, 41, 59 to 62, (1965).

Primary Examiner—Helen M. S. Sneed

[57] ABSTRACT

The reaction product obtained by combining (i) a titanate $(R^1O)_4Ti$ (particularly tetraisopropyl titanate) with (ii) a lower alkyl acetoacetate (particularly ethyl acetoacetate) and (iii) a substance which is either (a) at least one other titanate $(R^2O)_4Ti$ (particularly tetramethyl or tetra-n-butyl titanate or mixtures thereof) or (b) at least one alcohol $R^3OH$ (particularly methanol or n-butanol or mixtures thereof) wherein $R^2$ and $R^3$ differ from $R^1$ and are each methyl, isopropyl, n-butyl or n-pentyl and the titanate:acetoacetate mol ratio is in the range between 1:1 and 1:2 (preferably 1:1). The quantity of said substance is sufficient, even in the presence of a nucleating agent, to depress the freezing point of the reaction product obtained by combining said first-mentioned titanate with said acetoacetate. Also methods of preparing the reaction product are disclosed.

16 Claims, No Drawings

TITANATE COMPOSITIONS HAVING DEPRESSED FREEZING POINTS

BACKGROUND OF THE INVENTION

The present invention relates to a reaction product of a titanate and an acetoacetate which has been modified so as to lower its freezing point.

It has long been known that titanium esters react with high molecular weight hydroxyl-containing compounds so as to cross-link them and produce gels; J. Oil and Colour Chem. Assoc. 31, 405 (1948). However, the cross-linking reaction made through the use of simple alkyl esters of titanium proceeds too rapidly for most industrial uses. The cross-linking rate imparted by titanium esters can be depressed by combining a titanium ester with a variety of multifunctional compounds including an acetoacetate; U.S. Pat. No. 2,680,108 and Feld & Cowe, The Organic Chemistry of Titanium, published by Butterworth (1965). It should be noted that there is disagreement as to the structure of the complexes or chelates so-formed; cf. the structure given in the patent with that given by Yamamoto et al., J.A.C.S. 79 (1957), 4344-8.

The reaction product of tetraisopropyl titanate (also known as tetraisopropoxytitanium) and ethyl acetoacetate, at a titanate:acetoacetate mol ratio of 1:2, finds industrial use in cross-linking high molecular weight compounds. In that commercial reaction product, the isopropanol liberated in the reaction is removed, e.g., by distillation. That reaction product is normally a liquid, and sometimes it remains in the liquid state even after having been supercooled to some considerable extent. However, in the supercooled state, it sometimes spontaneously freezes, especially in the presence of a nucleating agent, such as dust or a part of the reaction product in crystal form. The reaction product of tetraisopropyl titanate and ethyl acetoacetate at a 1:1 mol ratio has an even greater tendency to freeze; when seeded with crystals of that reaction product, it may even freeze solid at room temperature (about 20°-25° C.).

SUMMARY OF THE INVENTION

The present invention provides a titanium composition, the freezing point of which has been depressed without adversely affecting its utility in cross-linking high molecular weight compounds. The present invention also provides processes by which to prepare the compositions of the present invention. The composition of the present invention comprises the reaction product of a titanium ester with a lower alkyl acetoacetate and either at least one other titanium ester or at least one alcohol which provides an alkoxy radical differing from that present in the original titanium ester.

DETAILED DESCRIPTION OF THE INVENTION

In particular, the composition of the present invention comprises the reaction product obtained by combining (i) a titanate represented by the empirical formula $(R^1O)_4Ti$ with (ii) an acetoacetate represented by the empirical formula

and (iii) a substance which is either (a) at least one other titanate represented by the empirical formula $(R^2O)_4Ti$ or (b) at least one alcohol represented by the empirical formula $R^3OH$ wherein the titanate:acetoacetate mol ratio is in the range between 1:1 and 1:2;
R is alkyl containing 1 to 4 carbons;
$R^2$ and $R^3$ differ from $R^1$; and
$R^1$, $R^2$ and $R^3$ are each methyl, isopropyl, n-butyl or n-pentyl.

The quantity of substance (a) or (b) is sufficient, even in the presence of a nucleating agent, to depress the freezing point of the reaction product obtained by combining the first-mentioned titanate with the acetoacetate.

The preferred reaction product is that obtained by combining a tetraalkyl titanate with ethyl acetoacetate, at a titanate:acetoacetate mol ratio between 1:1 and 1:2, and one or more alcohols. In one such embodiment, tetraisopropyl titanate is reacted with ethyl acetoacetate, at a mol ratio between 1:1 and 1:2, all or part of the isopropanol thereby generated is removed by distillation, and one or more of the $R^3OH$ alcohols other than isopropanol is added to the reaction product. The concentration of titanium in the final product is preferably substantially the same as in the reaction product of the first-mentioned titanium ester and ethyl acetoacetate.

In a more preferred embodiment, tetraisopropyl titanate is reacted with ethyl acetoacetate, at a titanate:acetoacetate mol ratio of 1:1; all of the isopropanol thereby generated is removed by distillation and a mixture of methanol and n-butanol is added in a quantity sufficient on a molar basis to replace the isopropanol which has been removed (Yamamoto et al., supra, report tetra-n-butyl titanate to be noncrystalline). The most preferred composition is that which contains about 51 mol % isopropoxy, about 11 mol % n-butoxy and about 38 mol % methoxy (Example 3). In similar embodiments, one can substitute other titanates for tetraisopropyl titanate, e.g., tetramethyl titanate (sometimes called titanium methoxide), tetra-n-butyl titanate, or the like, and alcohols other than methanol or n-butanol respectively.

The reaction of $(R^1O)_4Ti$ and one or more $(R^2O)_4Ti$ with an alkyl acetoacetate is exothermic. The reaction can be run at a temperature between room temperature and reflux temperature; i.e., about 20°-85° C. If one wishes to conduct the reaction at the lower end of that temperature range, one may do it either by providing a cooling means or by adding the titanate to the acetoacetate at a slow enough rate that the temperature remains in the lower portion of the range, e.g., 20°-50° C. $R^1OH$, liberated in that reaction, is removed. When that reaction product is to be reacted with one or more $R^3OH$, usually the amount of $R^1OH$ that is removed is substantially the same on a molar basis as the amount of $R^3OH$ being used. Most often the $R^1OH$ will be removed before adding $R^3OH$. However, it is not always necessary to do so; e.g., one can remove $R^1OH$ by distillation if the boiling point of $R^3OH$ is sufficiently higher than that of $R^1OH$.

In attempting to modify the reaction product of the titanate and alkyl acetoacetate so as to lower its freezing point, one is hampered by the tendency of such compositions to supercool for long periods of time without showing any tendency to freeze. Only by exposing the modified reaction product to lower temperature in the presence of seed crystals can one be certain that the freezing point of the modified reaction product has truly been reduced significantly.

In the examples that follow, the compositions of the invention are characterized as to mol percentage alkoxy content and temperature characteristics. The former is obtained by calculating the mol percentage of each individual alkoxy radical in the sum of the mols of alkoxy radicals provided by $(R^1O)_4Ti$ and $(R^2O)_4Ti$ or by $(R^1O)_4Ti$ and $R^3OH$. The latter is determined by holding the compositions at about $-25°$ C. for at least 4 hours, and usually overnight (about 16 hours), and thereafter seeding an aliquot of the composition with crystals of the reaction product of $(R^1O)_4Ti$ and alkyl acetoacetate. Thereafter, the compositions are inspected periodically to determine whether the composition has frozen, and if so, how long after seeding it occurred. If a composition freezes at $-25°$ C., it is then observed at $+2°$ C. and, if necessary, at room temperature (20°-25° C.) to determine if and when it becomes liquid.

EXAMPLE 1

A flask, vented through a reflux condenser and a bubble trap, was provided with a nitrogen atmosphere so as to exclude atmospheric moisture. To the flask were added 520 g of ethyl acetoacetate (about 4 mols). Taking care so as to give minimal exposure to atmospheric moisture, 568 g of tetraisopropyl titanate (about 2 mols) were transferred to a dropping funnel having a pressure equalizing tube, and from that dropping funnel with stirring to the flask. The titanate was added slowly to the ethyl acetoacetate so as to maintain the temperature in the range between 20° and 50° C. After stirring for one hour, the reaction product was transferred to a single neck flask and isopropanol was removed by distillation to a final condition of 40°-50° C. and 40-50 mm Hg so as to given a composition weighing 968 lg (had all of the isopropanol been removed, a reaction product weighing about 848 g would have been obtained). That composition was divided into 8 aliquots of 121 g containing 0.25 mol of titanium. To one of them, 29 g of isopropanol were added so as to provide a control. All other aliquots were made up to 150 g by the addition of various alcohols. The aliquots were cooled to about $-25°$ C. and seeded with solid particles of the reaction product of one mol of tetraisopropyl titanate and ethyl acetoacetate (1:2 titanate:acetoacetate mol ratio). After being exposed at $-25°$ C. for about ten days, samples were examined. Solid samples were thereafter exposed to $+2°$ C. for several days and then if necessary at room temperature (20°-25° C.). Table I sets forth the composition of the aliquots in terms of their mol percentage alkoxy content and describes their condition at various temperatures.

TABLE I

| Example (Aliquot) | Alkoxy Content | | Temperature Characteristics | | |
|---|---|---|---|---|---|
| | | | −25° C. | +2° C. | Room Temperature |
| 1 (A) | 47% Isopropoxy - | 53% Methoxy | 60 Vol. % Fluid | Fluid | — |
| 1 (B) | 68% Isopropoxy - | 32% Methoxy | Solid | 60 Vol. % Fluid | Fluid |
| 1 (C) | 56% Isopropoxy - | 44% Ethoxy | Solid | Solid | Fluid |
| 1 (D) | 75% Isopropoxy - | 25% Ethoxy | Solid | 60 Vol. % Solid | Fluid |
| 1 (E) | 67% Isopropoxy - | 33% n-Butoxy | Fluid | — | — |
| 1 (F) | 83% Isopropoxy - | 17% n-Butoxy | Solid | Fluid | — |
| 1 (G) | 31% Isopropoxy - | 14% n-Butoxy- 31% Methoxy | 70 Vol. % Solid | Fluid | — |
| Control | 100% Isopropoxy | | Solid | Solid | Fluid |

EXAMPLE 2

Example 1 was repeated with 260 g of ethyl acetoacetate (about 2 mols) and 568 g of tetraisopropyl titanate (about 2 mols). The resulting reaction product was distilled to a final condition of 40°-50° C. and 40-50 mm Hg and a weight of 710 g (theory 708), and divided into 8 aliquots of 88.8 g each. Each aliquot was made up to 121 g by the addition of various alcohols (isopropanol for the control) so as to give the compositions having the temperature characteristics set forth in Table II.

TABLE II

| Example (Aliquot) | Alkoxy Content | | Temperature Characteristics | | |
|---|---|---|---|---|---|
| | | | −25° C. | +2° C. | Room Temperature |
| 2 (A) | 43% Isopropoxy - | 57% Methoxy | Solid | Solid | 80 Vol. % Solid |
| 2 (B) | 51% Isopropoxy - | 49% Ethoxy | Solid | Solid | 95 Vol. % Solid |
| 2 (C) | 63% Isopropoxy - | 37% n-Butoxy | Solid | Solid | Fluid |
| 2 (D) | 63% Isopropoxy - | 37% 2-Methyl-propoxy | Solid | Solid | 90 Vol. % Solid |
| 2 (E) | 67% Isopropoxy - | 33% n-Pentoxy | Solid | Solid | Fluid |
| 2 (F) | 50% Isopropoxy - | 35% Methoxy- 15% n-Butoxy | Fluid | — | — |
| 2 (G) | 76% Isopropoxy - | 17% Methoxy- 7% n-Butoxy | Fluid | — | — |

TABLE II-continued

| Example (Aliquot) | Alkoxy Content | Temperature Characteristics | | |
| --- | --- | --- | --- | --- |
| | | −25° C. | +2° C. | Room Temperature |
| Control | 100% Isopropoxy | Solid | Solid | Solid |

EXAMPLE 3

The procedure of Example 2 was repeated with 2272 g of tetraisopropyl titanate (about 8 mols) and 1040 g of ethyl acetoacetate (about 8 mols) with stirring for one hour at a temperature of 70° C. or less (no heating or cooling was supplied). Isopropanol was removed to a final condition of 50°–60° C. and 40–50 mm Hg to give a composition weighing 2832±10 g, to which was added 604 g of methanol and 404 g of n-butanol. The resulting reaction product had an alkoxy content (exclusive of any contributed by the ethyl acetoacetate) of 51 mol % isopropoxy, 38 mol % methoxy and 11 mol % n-butoxy. When seeded and tested as described above at −25° C., no freezing was evident even after 10 days.

EXAMPLE 4

Example 1 was repeated except that isopropanol was removed by distillation so as to give a composition weighing 848 g. Table III sets forth the composition of the aliquots in terms of their mol percentage alkoxy content and describes their condition at various temperatures.

TABLE III

| Example (Aliquot) | Alkoxy Content | | Temperature Characteristics | | |
| --- | --- | --- | --- | --- | --- |
| | | | −25° C. | +2° C. | Room Temperature |
| 4 (A) | 44% Isopropoxy - | 56% Methoxy | Solid | 60 Vol. % Solid | Fluid |
| 4 (B) | 27% Isopropoxy - | 73% Methoxy | 40 Vol. % Solid | Fluid | — |
| 4 (C) | 53% Isopropoxy - | 47% Ethoxy | Solid | 75 Vol. % Solid | Fluid |
| 4 (D) | 34% Isopropoxy - | 66% Ethoxy | Solid | 75 Vol. % Solid | Fluid |
| 4 (E) | 64% Isopropoxy - | 36% n-Butoxy | Fluid | — | — |
| 4 (F) | 46% Isopropoxy - | 54% n-Butoxy | Fluid | — | — |
| 4 (G) | 34% Isopropoxy - | 20% n-Butoxy- 46% Methoxy | Fluid | — | — |
| Control | 100% Isopropoxy | | Solid | Solid | Fluid |

I claim:

1. A composition comprising the reaction product obtained by reacting (i) a titanate represented by the empirical formula $$(R^1O)_4Ti$$

with (ii) an acetoacetate and removing all or part of the $R^1OH$ thereby generated and replacing all or part of it by combining the resulting titanate/acetoacetate reaction product with (iii) a substance which is either (a) at least one other titanate represented by the empirical formula $$(R^2O)_4Ti$$

or (b) at least one alcohol represented by the empirical formula $$R^3OH$$

wherein the titanate:acetoacetate mol ratio is in the range between 1:1 and 1:2;

$R^2$ and $R^3$ differ from $R^1$; and $R^1$, $R^2$ and $R^3$ are each methyl, ethyl, 2-chloroethyl, isopropyl, n-propyl, n-butyl, n-pentyl, 2-pentyl, 3-methylbutyl, 2-methoxyethyl, or methoxyethoxyethyl;

the quantity of said substance being sufficient, even in the presence of a nucleating agent, to depress the freezing point of the reaction product obtained by combining said first-mentioned titanate with acetoacetate.

2. The composition of claim 1 wherein said substance is at least one alcohol represented by the empirical formula $$R^3OH.$$

3. The composition of claim 1 wherein the titanate represented by the empirical formula $$(R^1O)_4Ti$$

is tetraisopropyl titanate.

4. The composition of claim 3 wherein said substance is at least one alcohol represented by the empirical formula $$R^3OH.$$

5. The composition of claim 4 wherein said substance comprises methanol.

6. The composition of claim 4 wherein said substance comprises n-butanol.

7. The composition of claim 4 wherein said substance comprises a mixture of methanol and n-butanol.

8. The composition of claim 7 in which the $(R^1O)_4Ti$:acetoacetate mol ratio is 1:1.

9. The composition of claim 8 which contains about 51 mol % isopropoxy, about 11 mol % n-butoxy and about 38 mol % methoxy substituents.

10. A process for depressing the freezing point of a titanate/acetoacetate reaction product which comprises reacting (i) a titanate represented by the empirical formula $$(R^1O)_4Ti$$

with (ii) an acetoacetate and removing all or part of the $R^1OH$ thereby generated and replacing all or part of it by combining the resulting titanate/acetoacetate reaction product with (iii) a substance which is either (a) at least one other titanate represented by the empirical formula $$(R^2O)_4Ti$$

or (b) at least one alcohol represented by the empirical formula $$R^3OH$$

wherein the titanate:acetoacetate mol ratio is in the range between 1:1 and 1:2;

$R^2$ and $R^3$ differ from $R^1$; and $R^1$, $R^2$ and $R^3$ are each methyl, ethyl, 2-chloroethyl, isopropyl, n-propyl, n-butyl, n-pentyl, 2-pentyl, 3-methylbutyl, 2-methoxyethyl, or methoxyethoxyethyl;

the quantity of said substance being sufficient, even in the presence of a nucleating agent, to depress the freezing point of the reaction product obtained by combining said first-mentioned titanate with acetoacetate.

11. The process of claim 10 wherein said substance is at least one alcohol represented by the empirical formula $$R^3OH.$$

12. The process of claim 10 in which said titanate represented by the empirical formula $$(R^1O)_4Ti$$

is tetraisopropyl titanate.

13. The process of claim 12 wherein tetraisopropyl titanate is reacted with ethyl acetoacetate, all or part of the isopropanol thereby generated is removed from the reaction product and one or more of the alcohols represented by the empirical formula $$R^3OH$$

is added to the reaction product.

14. The process of claim 13 wherein the titanate:ethyl acetoacetate mol ratios is 1:1, substantially all of the isopropanol is removed by distillation and a mixture of methanol and n-butanol is added in a quantity sufficient to replace the isopropanol which has been removed.

15. The process of claim 11 wherein an alcohol represented by the empirical formula $$R^1OH,$$

generated in the reaction of said acetoacetate and the titanate represented by the empirical formula $$(R^1O)_4Ti,$$

is substantially removed prior to the introduction of at least one alcohol represented by the empirical formula $$R^3OH.$$

16. The process of claim 11 wherein the alcohol represented by the empirical formula $$R^1OH$$

generated in the reaction of said acetoacetate and the titanate represented by the empirical formula $$(R^1O)_4Ti$$

has a lower boiling point than the alcohol represented by the empirical formula $$R^3OH$$

and the alcohol represented by the empirical formula $$R^1OH$$

is substantially removed after completion of the reaction of said acetoacetate, said titanate and said alcohol represented by the empirical formula $$R^3OH.$$

* * * * *